US008673902B2

(12) United States Patent
Cagle et al.

(10) Patent No.: US 8,673,902 B2
(45) Date of Patent: *Mar. 18, 2014

(54) METHOD OF TREATING OTIC INFECTIONS WITH MOXIFLOXACIN COMPOSITIONS

(75) Inventors: Gerald Cagle, Fort Worth, TX (US); Robert L. Abshire, Fort Worth, TX (US); David W. Stroman, Irving, TX (US); John M. Yanni, Burleson, TX (US)

(73) Assignee: Alcon Pharmaceuticals, Ltd., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/611,510

(22) Filed: Nov. 3, 2009

(65) Prior Publication Data
US 2010/0048522 A1 Feb. 25, 2010

Related U.S. Application Data

(63) Continuation of application No. 10/715,055, filed on Nov. 17, 2003, now Pat. No. 7,671,070, which is a continuation of application No. 10/200,868, filed on Jul. 22, 2002, now Pat. No. 6,716,830, which is a continuation of application No. 09/646,797, filed as application No. PCT/US99/22622 on Sep. 29, 1999, now abandoned.

(60) Provisional application No. 60/102,504, filed on Sep. 30, 1998, provisional application No. 60/102,506, filed on Sep. 30, 1998.

(51) Int. Cl.
A61K 31/353 (2006.01)

(52) U.S. Cl.
USPC .................................................. 514/230.5

(58) Field of Classification Search
USPC .................................................. 514/230.5
See application file for complete search history.

(56) References Cited

U.S. PATENT DOCUMENTS

| 4,474,751 | A | 10/1984 | Haslam et al. |
| 4,551,456 | A | 11/1985 | Katz |
| 4,670,444 | A | 6/1987 | Grohe et al. |
| 4,710,495 | A | 12/1987 | Bodor |
| 4,730,013 | A | 3/1988 | Bondi et al. |
| 4,844,902 | A | 7/1989 | Grohe |
| 4,920,120 | A | 4/1990 | Domagala et al. |
| 4,980,470 | A | 12/1990 | Masuzawa et al. |
| 4,990,517 | A | 2/1991 | Petersen et al. |
| 4,996,335 | A | 2/1991 | Bodor |
| 5,059,597 | A | 10/1991 | Petersen et al. |
| 5,149,693 | A | 9/1992 | Cagle et al. |
| 5,149,694 | A | 9/1992 | Cagle et al. |
| 5,164,402 | A | 11/1992 | Brighty |
| 5,185,337 | A | 2/1993 | Fujii et al. |
| 5,223,493 | A | 6/1993 | Boltralik |
| 5,416,096 | A | 5/1995 | Petersen et al. |
| 5,480,879 | A | 1/1996 | Petersen et al. |
| 5,520,920 | A | 5/1996 | Castillo et al. |
| 5,540,930 | A | 7/1996 | Guy et al. |
| 5,563,138 | A | 10/1996 | Ueda et al. |
| 5,597,560 | A | 1/1997 | Bergamini et al. |
| 5,607,942 | A | 3/1997 | Petersen et al. |
| 5,631,004 | A | 5/1997 | Cagle et al. |
| 5,665,373 | A | 9/1997 | Robertson et al. |
| 5,679,665 | A | 10/1997 | Bergamini et al. |
| 5,849,752 | A | 12/1998 | Grunenberg et al. |
| 5,854,241 | A | 12/1998 | Hallenbach et al. |
| 5,912,255 | A | 6/1999 | Bussell |
| 6,093,417 | A | 7/2000 | Petrus |
| 6,395,746 | B1 | 5/2002 | Cagle et al. |
| 6,440,964 | B1 | 8/2002 | Cagle et al. |
| 6,509,327 | B1 | 1/2003 | Cagle et al. |
| 6,716,830 | B2 | 4/2004 | Cagle et al. |
| 6,740,664 | B2 | 5/2004 | Cagle et al. |
| 2006/0074053 | A1 | 4/2006 | Asada et al. |
| 2006/0183698 | A1 | 8/2006 | Abelson |
| 2006/0276777 | A1 | 12/2006 | Coroneo |
| 2007/0049552 | A1 | 3/2007 | Babu et al. |

FOREIGN PATENT DOCUMENTS

| CA | 2086914 | 7/1993 |
| EP | 0550903 A | 7/1993 |
| EP | 0 982 031 | 3/2000 |
| EP | 1 025 846 | 8/2000 |
| ES | 08320 | 4/1993 |
| WO | 9001933 A | 3/1990 |
| WO | WO 90/01933 | 3/1990 |
| WO | 9639146 A | 12/1996 |
| WO | WO 96/39146 | 12/1996 |
| WO | WO 98/06435 | 2/1998 |
| WO | WO 99/15172 | 4/1999 |

(Continued)

OTHER PUBLICATIONS

"Plaintiffs Alcon, Inc.'s and Alcon Manufacturing, Ltd.'s Responsive Interrogatory Concerning Defendant's Supplemental § 112, ¶ 1 Defenses," (Jan. 22, 2008) Bayer Healthcare AG, Alcon, Inc., and Alcon Research, Ltd. v. Teva Pharmaceuticals USA, Inc. (Civil Action No. 06-234 SLR).
"Defendant's Supplemental Responses to Plaintiffs' Interrogatories Nos. 3, 7-9, 16, 18, 23, and 24," (Nov. 27, 2007) Bayer Healthcare AG, Alcon, Inc., and Alcon Research, Ltd. v. Teva Pharmaceuticals USA, Inc. (Civil Action No. 06-234 SLR).
Pawar et al., AAPS PharmSciTech, 7(1), E1-E6 (2006), "Effect of Formulation Factors on In Vitro Permeation of Moxifloxacin From Aqueous Drops Through Excised Goat, Sheep, and Buffalo Corneas".
Chan et al., Anal. Bochem., 353, 30-36 (2006), "Determinaton of ofloxacin and moxifloxacin and their penetration in human aqueous and vitreous humor by using high-performance liquid chromatography fluorescence detection".

(Continued)

Primary Examiner — Zohreh Fay
(74) Attorney, Agent, or Firm — Banner & Witcoff, Ltd.

(57) ABSTRACT

Ophthalmic, otic and nasal compositions containing a new class of antibiotics (e.g., moxifloxacin) are disclosed. The compositions preferably also contain one or more anti-inflammatory agents. The compositions may be utilized to treat ophthalmic, otic and nasal conditions by topically applying the compositions to the affected tissues.

9 Claims, No Drawings

(56) References Cited

FOREIGN PATENT DOCUMENTS

| WO | 0001365 | 1/2000 |
|---|---|---|
| WO | WO 00/18386 | 4/2000 |
| WO | WO 00/18387 | 4/2000 |
| WO | WO 00/18388 | 4/2000 |
| WO | WO 00/18404 | 4/2000 |
| WO | WO 01/45679 | 6/2001 |
| WO | WO 01/89495 | 11/2001 |

OTHER PUBLICATIONS

Expert Report of Eduardo C. Alfonso, M.D. (43 pages; dated Sep. 19, 2007) in *Bayer Healthcare AG, Alcon, Inc., and Alcon Research, Ltd. v. Teva Pharmaceuticals USA, Inc.* (Civil Action No. 06-234 (SLR)).
Expert Repor of Ashim K. Mitra, Ph.D. (27 pages; dated Sep. 19, 2007) in *Bayer Healthcare AG, Alcon, Inc., and Alcon Research, Ltd. v. Teva Pharmaceuticals USA, Inc.* (Civil Action No. 06-234 (SLR)).
Expert Report of George G. Zhanel, Ph.D. (66 pages; dated Sep. 19, 2007) in *Bayer Healthcare AG, Alcon, Inc., and Alcon Research, Ltd. v. Teva Pharmaceuticals USA Inc.* (Civil Action No. 06-234 (SLR)).
Gennaro, Alfonso, R., "19th Edition, Remington: Practice of The Science & Pharmacy, 1995" Ophthalmic Preparations, Chapter 89, pp. 1563-1576.
Trial Transcript for Feb. 28, 2008 for *Bayer Healthcare AG, Alcon, Inc., and Alcon Research, Ltd. v. Teva Pharmaceuticals USA, Inc.* (Civil Action No. 06-234 (SLR)).
Trial Transcript for Mar. 3, 2008 for *Bayer Healthcare AG, Alcon, Inc., and Alcon Research, Ltd. v. Teva Pharmaceuticals USA, Inc.* (Civil Action No. 06-234 (SLR)).
Trial Transcript for Mar. 4, 2008 for *Bayer Healthcare AG, Alcon, Inc., and Alcon Research, Ltd. v. Teva Pharmaceuticals USA, Inc.* (Civil Action No. 06-234 (SLR)).
Trial Transcript for Mar. 5, 2008 for *Bayer Healthcare AG, Alcon, Inc., and Alcon Research, Ltd. v. Teva Pharmaceuticals USA, Inc.* (Civil Action No. 06-234 (SLR)).
Trial Transcript for Mar. 6, 2008 for *Bayer Healthcare AG, Alcon, Inc., and Alcon Research, Ltd. v. Teva Pharmaceuticals USA, Inc.* (Civil Action No. 06.234 (SLR)).
USP Dictionary of USAN and International Drug Names (2000 edition), p. 479, from List of Exhibits to Expert Report of Dr. Loyd V. Allen, Jr.
Monograph for Vigamox from the 61st edition of the Physician's Desk Reference, published in 2007, from List of Exhibits to Expert Report of Dr. Loyd V. Allen, Jr.
Modern Pharmaceutics, 2nd ed. (1990), Ch. 14: Design and Evaluation of Ophthalmic Pharmaceutical Products (Marcel Dekker, Inc., New York), from List of Exhibits to Expert Report of Dr. Loyd V. Allen, Jr.
Tierney et al., eds., Current Medical Diagnosis & Treatment, 37th ed. (1998), pp. 186, from List of Exhibits to Expert Report of Dr. Loyd V. Allen, Jr.
Entry for "Ciloxan Solution/Drops; Ophthalmic" in the U.S. Food and Drug Administration's Approved Drug Products with Therapeutic Equivalence Evaluations; from List of Exhibits to Expert Report of Dr. Loyd V. Allen, Jr.
Monograph for Ciloxan from the 53rd edition of the Physician's Desk Reference, published in 1999, from List of Exhibits to Expert Report of Dr. Loyd V. Allen, Jr.
Firestone et al., "Solubility characteristics of three fluoroquinolone ophthalmic solutions in an in vitro tear model," Int J. Pharm 164 (1998) 119-128, from List of Exhibits to Expert Report of Dr. Loyd V. Allen, Jr.
Poster entitled "Synthesis and In Vitro Activity of BAY12-8039, a New 8-Methoxyquinolone" from List of Exhibits to Expert Report of Dr. Loyd V. Allen, Jr.
Abstract entitled "Synthesis and In Vitro Activity of BAY12-8039, a New 8-Methoxyquinolone,"with associated documents from List of Exhibits to Expert Report of Dr. Loyd V, Allen, Jr.
Monograph for Ciloxan from the 50th edition of the Physicians' Desk Reference, published in 1996, from List of Exhibits to Expert Report of Dr. Loyd V. Allen, Jr.
Monograph for Tobradex Ophthalmic Suspension from the 50th edition of the physicians' Desk Reference, published in 1996, from List of Exhibits to Expert Report of Dr. Loyd V. Allen, Jr.
Entry for "Ciloxan Ointment; Ophthalmic" in the U.S. Food and Drug Administration's Approved Drug Products with Therapeutic Equivalence Evaluations, from List of Exhibits to Expert Report of Dr. Loyd V. Allen, Jr.
Franz-Josef Schmitz et al., "Relationship between ciprofloxacin, ofloxacin, levofloxacin, sparfloxacin and moxifloxacin (BAY 12-8039) MICs and mutations in grlA, grlB, gyrA and gyrB in 116 unrelated clinical isolates of *Staphylococcus aureus*," Journal of Antimicrobial Chemotherapy (1998) 41, 481-484.
A. Dalhoff et al, "In vitro Activity of BAY 12-8039, a New 8-Methoxyquinolone,"Chemotherapy 1996; 42; 410-425, Plaintiff's Exhibit 1124; Deposition Exhibit D-124 Nov. 15, 2007.
Deposition of David W. Stroman, Ph.D, Jun. 21, 2007, *Bayer Healthcare AG, Alcon, Inc., and Alcon Research, Ltd. v. Teva Pharmaceuticals USA, Inc.* (Civil Action No. 06-234 SLR).
Defendant's Supplemental Notice Pursuant to 35 U.S.C. § 282, Jan. 25, 2008, *Bayer Healthcare AG, Alcon, Inc., and Alcon Research, Ltd. v. Teva Pharmaceuticals USA, Inc.* (Civil Action No. 06-234 SLR).
PTX0059: Confidential letter dated Feb. 21, 2006 regarding Patent Certification Notice—U.S. Patent Nos. 4,990,517, 5,607,94PTX0059: Confidential letter dated Feb. 21, 2006 regarding Patent Certification Notice—U.S. Patent Nos. 4,990,517, 5,607,942, and 6,716,830 Moxifloxacin Hydrochloride Ophthalmic Solution, 0.5% as base, Teva Pharmaceuticals USA, Inc.'s ANDA 78-073, 20 pages, in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0163: EP Application 0195316 A1, Irikura et al., Quinolonecarboxylic Acid Derivatives (Kyorin) (RT001-012950-012993) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0171: Curriculum Vitae of Dr. George G. Zhanel in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0184-D: Chaudhry et al., Scleral Buckle Infection with Ciprofloxacin-Resistant *Pseudomonas aeruginosa*, Arch. Ophthalmol., 116:1251 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0189: Chaudhry et al., Emerging Ciprofloxacin-Resistant *Pseudomonas aeruginosa*, Am. J. Ophthalmology, 128 (4):509-10 (1999) in *Bayer Healthcare AG, Alcon, Inc., and Alcon Research, Ltd. v. Teva Pharmaceuticals USA, Inc.* (Civil Action No. 06-234 SLR) (Plaintiffs Exhibit List).
PTX0194-D: Ball et al., Therapeutic Advances of New Fluoroquinolones, Expert Opinion on Investigational Drugs, 7 (5):761-83 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0209: Leophonte et al., Trovafloxacin Versus Amoxicillin/ Clavulanic Acid in the Treatment of Acute Exacerbations of Chronic Obstructive Bronchitis, Eur. J. Clin. Microbicol, Infect. Dis., 17:434-40 (1998) in *Bayer Healthcare AG, Alcon, Inc., and Alcon Research, Ltd. v. Teva Pharmaceuticals USA, Inc.* (Civil Action No. 06-234 SLR) (Plaintiffs Exhibit List).
PTX2030I: Powerpoint slide: Some Compounds are Maintained Longer in the Aqueous Humor in *Bayer Healthcare AG, Alcon, Inc., and Alcon Research, Ltd. v. Teva Pharmaceuticals USA, Inc.* (Civil Action No. 06-234 SLR).
PTX2031A: Powerpoint slide: Moxifloxacin in Solution in *Bayer Healthcare AG, Alcon, Inc., and Alcon Research, Ltd. v. Teva Pharmaceuticals USA, Inc.* (Civil Action No. 06-234 SLR).
PTX2031B: Powerpoint slide: Moxifloxacin in Solution in *Bayer Healthcare AG, Alcon, Inc., and Alcon Research, Ltd. v. Teva Pharmaceuticals USA, Inc.* (Civil Action No. 06-234 SLR).
Communication of a Notice of Opposition (from EP Patent Office) dated Aug. 23, 2004, Opposition against EP Patent 1117401.

(56) References Cited

OTHER PUBLICATIONS

Declaration of David W. Stroman, Ph.D., Opposition against EP Patent 1117401.
Communication dated Jun. 28, 2005 from European Patent Office regarding Opposition against EP Patent 1117401.
Summons to attend oral proceedings in Opposition against EP Patent 1117401.
Communication dated Jul. 12, 2006 from European Patent Office regarding Opposition against EP Patent 1117401.
Notification dated Jul. 14, 2006 from European Patent Office regarding Opposition against EP Patent 1117401, which includes a letter from the opponent dated Jul. 11, 2006.
Letter from opponent dated Jul. 28, 2006 regarding Opposition against EP Patent 1117401.
Complaint filed Apr. 5, 2006 in *Bayer Healtchare AG, Alcon, Inc., and Alcon Manufacturing Ltd. v. Teva Pharmaceuticals, USA, Inc.* (C.A. No. 06-234).
Letter from TEVA to Bayer Healthcare and Bayer Healthcare AG dated Feb. 21, 2006 regarding Patent Certification Notice—U.S. Patents 4,990,517; 5607,942; and 6,716,830.
Answer and Defenses of Defendant Teva Pharmaceuticals USA, Inc. dated Apr. 28, 2006 *Bayer Healtchare AG, Alcon, Inc., and Alcon Manufacturing Ltd. v. Teva Pharmaceuticals, USA, Inc.* (CA No. 06-234 (SLR)).
Survey of Ophthalmology, vol. 50, Supplement 1, Nov. 2005.
Arch Ophthalmol /vol. 123, Sep. 2005, pp. 1282-1283.
Ophthalmology, vol. 112, No. 11, Nov. 2005, pp. 1992-1996.
Ophthalmology, vol. 113, No. 6, Jun. 2006, pp. 955-959.
Survey of Ophthalmology, vol. 50, Supplement 1, Nov. 2005, pp. 55-63.
Current Medical Research and Opinion, vol. 21, No. 1, 2005, pp. 93-94.
Ophthalmology, vol. 112, No. 3, Mar. 2005, pp. 466-469.
Who Drug Information, vol. 11, No. 4, 1997 pp. 265-266 and 79.
Decision Rejecting Opposition, dated Oct. 30, 2006 for EP 99 956 504.7.
Provision of the minutes in accordance with Rule 76(4) EPC, dated Oct. 30, 2006, for EP 99 956 504.7.
Expert Report of Dr. Loyd V. Allen, Jr., executed Jul. 26, 2007, along with 19 Exhibits, *Bayer Healthcare AG, Alcon, Inc., and Alcon Manufacturing, Ltd. v. Teva Pharmaceuticals USA, Inc.* (Civil Action No. 06-234 SLR).
Defendant Teva Pharmaceuticals USA, Inc.'s Answering Post-Trial Brief on Teva's Noninfringement of Claim 1 of the '830 Patent, *Bayer Healthcare AG, Alcon, Inc. and Alcon Research, Ltd. v. Teva Pharmaceuticals USA, Inc.*, Civil Action No. 06-234 (SLR).
Defendant Teva Pharmaceuticals USA, Inc.'s Opening Post-Trial Brief on the Invalidity of U.S. Patent No. 6,716,830 (redacted), *Bayer Healthcare AG, Alcon, Inc. and Alcon Research, Ltd. v. Teva Pharmaceuticals USA, Inc.*, Civil Action No. 06-234 (SLR).
Plaintiff's Post-Trial Brief on Validity, *Bayer Healthcare AG, Alcon, Inc. and Alcon Research Ltd. v. Teva Pharmaceuticals USA, Inc.*, Civil Action No. 06-234 (SLR), dated Jul. 2, 2008.
Defendant Teva Pharmaceuticals USA, Inc.'s Post-Trial Reply Brief on the Invalidity of U.S. Patent No. 6,716,830, Civil Action No. 06-234 (SLR), dated Aug. 1, 2008.
Written Opinion of the EPO Board of Appeal in support of its revocation of Alcon's European Patent No. 1,117,401; European Case No. T 0015/07-3.3.02, Decision of the Technical Board of Appeal 3.3.02 of Apr. 30, 2009 (Case 1:06-cv-00234-SLR, Document 118-2, filed Jun. 19, 2009), 19 pages.
District Court's Opinion dated Oct. 19, 2009, *Alcon, Inc. and Alcon Research, Ltd. v. Teva Pharmaceuticals USA, Inc.* litigation, Civil. No. 06-234-SLR.
DTX0064: Email from Robert Abshire to Robert Hackett, Joe Hidemen, and David Stroman in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0068: Email from Barry A. Schlech, Ph.D., having the subject "Moxifloxacin Team Meeting Minutes—Thu, Apr. 20, 2000 (Training Room 10:30AM)" in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0069: Email from Gerald D. Cagle to Joe Hiddemen, Stella Robinson, Rajni Jani, Barry Schlech, Ed Dorsey, Henry Baldwin, William Hubregs, Sudhir Dave, Tom McDonald, and Michael Bergamini in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0137: Excerpt from the 61st Edition of the Physician's Desk Reference (2007), pp. 468-469, with cover page, copyright information, and table of contents excerpt in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0140: Tierney, et al., eds., Current Medical Diagnosis & Treatment, 37th ed. (1998), p. 186 in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0141. Entry for "Ciloxan Solution/Drops; Ophthalmic" in the U.S. Food and Drug Administration's Approved Drug Products with Therapeutic Equivalence Evaluations in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0144: Excerpt from the 50th Edition of the Physician's Desk Reference (1996), pp. 472-473, with cover page and copyright information in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0145: Excerpt from the 50th Edition of the Physician's Desk Reference (1996), pp. 473-474, with cover page and copyright information in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0146: Entry for "Ciloxan Ointment; Ophthalmic" in the U.S. Food and Drug Administration's Approved Drug Products with Therapeutic Equivalence Evaluations in *Bayer Healthcare AG, Alcon. Inc.. and Alcon Research, Ltd. v. Teva Pharmaceuticals USA, Inc.* (Civil Action No. 06-234 SLR) (Defendants' Exhibit List).
DTX0159: Monograph for Ocuflux from the 49th edition of the Physician's Desk Reference, pp. 496-497 in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0161: Al-Nawas, G., Shad P., Intracellular activity of ciprofloxacin and moxifloxacin, a new 8-methoxyquinolone, against methoicillin-resistant *Staphylococcus aureus*, J. Antimocrob Chemother, 41:655-658 (1998) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0170: Dalhoff, A., Lack of in vivo emergency of resistance against BAY 12-8039 in *S. aureus* and *S. pneumonia*. Abstract and Poster 47. 0003, p. 124 in Abstracts of the 8th International Congress on Infectious Diseases, Boston, Massachusetts. (1998) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0191: Ostergaard, C., et al., Evaluation of a new 8-methoxyquinolone—BAY-128039—against a penicillin-resistant *Streptococcus pneumonia* type 9V in experimental meningitis in rabbits. Abstracts and Poset B77, p. 40 in Program and abstracts of the 37th Interscience Conference on Antimicrobial Agents and Chemotherapy, Toronto, Canada (1997) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0195: Schmidt, H., et al., Moxifloxacin in therapy of experimental pneumococcal meningitis. Antimicrob Agents Chemother. 42: 1397-1401. (1998) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0202: Stass, H., et al., Pharmacokinetics, safety and tolerability of 800mg BAY 12-8039 administered orally as a single dose. 8 Eur Cong Clin Microbiol Inf Dis, lausanne, Switzerland, 1997, Abstr p.

(56) References Cited

OTHER PUBLICATIONS 388 (1997) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0209: Zhanel, G., et al., In vitro activities of six fluoroquinolones against Canadian isolates of vancomycin-sensitive and vancomycin-resistant *Enterococcus* species. Diag Microbiol Infect Dis 31:343-347. (1998) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0214: Kusjanto, Mantik, Bayer warns doctors on rare Avelox side effects, Reuters.com, (Feb. 14, 2008) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0238: Pijls, Rachel, et al., Studies on a new device for drug delivery to the eye. Eur. J. Pharm. Biopharm., 59:283-288 (2005) in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX0243: Entry for Labischinksi, H., et al., The targeting of factors necessary for expression of methicillin resistance in staphylococci in the J. Antimicrob. Chemother. 41(6) on http://jac.oxfordjournals.org/content/vol41/issue6/index.dtl in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4011: Demonstrative—Claim Charts in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4012: Demonstrative—Concentration ranges for '942 Patent in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4013: Demonstrative—Comparison of Ingredients Chart in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4014: Demonstrative—Comparison of Ingredients Chart in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4015: Demonstrative—Comparison of Ingredients Chart in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4016: Demonstrative—Comparison of Ingredients Chart in *Bayer Healthcare AG, Alcon, Inc., and Alcon Research, Ltd. v. Teva Pharmaceuticals USA, Inc.* (Civil Action No. 06-234 SLR) (Defendants' Exhibit List).
DTX4017: Demonstrative—Blowup of PTX 1098 in *Bayer Healthcare AG, Alcon, Inc., and Alcon Research, Ltd. v. Teva Pharmaceuticals USA, Inc.* (Civil Action No. 06-234 SLR) (Defendants' Exhibit List).
Defendants' Exhibit List (admitted to trial)—in *Bayer Healthcare AG, Alcon, Inc., and Alcon Research, Ltd. v. Teva Pharmaceuticals USA, Inc.* (Civil Action No. 06-234 SLR).
Exhibit 7—Defendants' Exhibit List in *Bayer Healthcare AG, Alcon, Inc., and Alcon Research, Ltd. v. Teva Pharmaceuticals USA, Inc.* (Civil Action No. 06-234 SLR).
Exhibit 6—Plaintiffs' Exhibit List in *Bayer Healthcare AG, Alcon, Inc., and Alcon Research, Ltd. v. Teva Pharmaceuticals USA, Inc.* (Civil Action No. 06-234 SLR).
Plaintiffs' Exhibit List (admitted to trial) in *Bayer Healthcare AG, Alcon, Inc., and Alcon Research, Ltd. v. Teva Pharmaceuticals USA, Inc.* (Civil Action No. 06-234 SLR).
Exhibit 3—Teva's Pretrial Statement in *Bayer Healthcare AG, Alcon, Inc., and Alcon Research, Ltd. v. Teva Pharmaceuticals USA, Inc.* (Civil Action No. 06-234 SLR).
Exhibit 5—Teva's Pretrial Statement in *Bayer Healthcare AG, Alcon, Inc., and Alcon Research, Ltd. v. Teva Pharmaceuticals USA, Inc.* (Civil Action No. 06-234 SLR).
Exhibit 11—Teva's Brief Statements of Intended Proofs in *Bayer Healthcare AG, Alcon, Inc., and Alcon Research, Ltd. v. Teva Pharmaceuticals USA, Inc.* (Civil Action No. 06-234 SLR).
European Office Action mailed Apr. 30, 2012 regarding EP Application No. 10.176412.4.
Kouppari, G. et al, "Aerobic Microorganisms Isolated From Children With Otorrhea", Deltion Ellenikes Mikrobiologikes Etaireias, vol. 34, No. 3, 1989, pp. 273-281.
Obi, C.L., et al. "Bacterial agents causing chronic suppurative otitis media", East African Medical Journal KE, vol. 72, No. 6, 1995, pp. 370-372.
Garcia-Martos P., et al., "Nosocomial infection by *Xanthomonas maltophilla*: Antimicrobial resistance profile," Revista Espanola De Quimioterapia 1995 ES, vol. 8, No. 2, 1995, pp. 137-140.
Rotimi V.O. et al., "The bacteriology of chronic suppurative otitis media.", East African Medical Journal, Jul. 1992, LNKD—PUBMED: 1396196, vol. 69, No. 7, Jul. 1992, pp. 394-397.
Thore M. et al., "Efficacy of Metronidazole in experimental Bacteroides fragilis otitis media.", Acta Oto-Laryngologica Jan.-Feb. 1985 LNKD—PUBMED: 3976396, vol. 99, No. 1-2, Jan. 1995, pp. 60-66.
Fairbanks, D.N., "Topical therapeutics for otitis media", Otolaryngology—Head and Neck Surgery: Official Journal of American Academy of Otolaryngology—Head and Neck Surgery May-Jun. 1981 LNKD—PUBMED: 6791095, vol. 89, No. 3 Pt 1, May 1981, pp. 381-385.
Cooper M.A. et al., "Ciprofloxacin Resistance Developing During Treatment of Malignant Otitis Externa.", The Journal of Antimicrobial Chemotherapy, Jul. 1993 LNKD—PUBMED: 8226407, vol. 32, No. 1, Jul. 1993.
PTX0086: Excerpt of Kathleen Alford's Lab Notebook (AL0022-000011-014) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0089: Alcon Research Compound Submission (AL007-023353) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0094: Bayer Data (BL002-024345-0024346) in *Bayer Healthcare AG, Alcon, Inc., and Alcon Research, Ltd. v. Teva Pharmaceuticals USA, Inc.* (Civil Action No, 06-234 SLR) (Plaintiffs' Exhibit List).
PTX0095: Bayer Data (BL002-029484) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0096: Bayer Data (BL002-030069) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0097: Bayer Data (BL002-031182-031183) in *Bayer Healthcare AG, Alcon, Inc and Alcon Research, Ltd. v. Teva Pharmaceuticals USA, Inc.* (Civil Action No. 06-234 SLR) (Plaintiffs' Exhibit List).
PTX101: Curruciulum Vitae of Loyd V. Allen, Ph.D. in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX115: Petersen et al., Synthesis and in vitro Activity of BAY 12-8039, A New 8-Methoxy-quinolone, 36th ICAAC (1996) (Abstract) (BL014-011453-011455) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0135: Klugman and Capper, Concentration-dependent Killing of Antibiotic-resistant Pneumococci by the Methoxyquinolone Moxifloxacin, J. Antimicrobial Chemotherapy, 40:797-02 (1997) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0136: Ostergaard et al., Evaluation of Moxifloxacin, a New 8-Methoxyquinolone, for Treatment of Meningitis Caused by a Penicillin-Resistant Pneumococcus in Rabbits, Antimicrobial Agents and Chemotherapy, 42: 1706-12 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).

(56) References Cited

OTHER PUBLICATIONS

PTX0137: Woodcock et al., In Vitro Activity of Bay 12-8039, A New Fluoroquinolone, Antimicrobial Agents and Chemotherapy, 41(1):101-06 (1997) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0210: O'Doherty et al., Treatment of Acute Exacerbations of Chronic Bronchitis: Comparison of Trovafloxacin and Amoxicillin in a Multicentre, Double-Blind, Double-Dummy Study, Eur. J. Clin. Microbiol. Infect. Dis., 17:441-46 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0212: Williams and Hopkins, Safety of Trovafloxacin in Treatment of Lower Respiratory Tract Infections, Eur. J. Clln. Microbiol. Infect. Dis., 17:454-58 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0214: FDA Issues Public Heath Advisory on Liver Toxicity Associated with the Antibiotic Trovan in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0215: Chodosh et al., Efficacy and Safety of a 10-Day Course of 400 or 600 Milligrams of Grepafloxacin Once Daily for Treatment of Acute Bacterial Exacerbations of Chronic Bronchitis: Comparison with a 10-Day Course of 500 Milligrams of Ciprofloxacin Twice a Day, Anti. Agents Chem., 42(1):114-20 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0218: Cormican and Jones, Antimicrobial Activity and Spectrum of LB20304, a Novel Fluoronaphthyridone, Anti. Agents Chem., 41(1):204-11 (1997) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0223: Stass et al., Pharmacokinetics, Safety, and Tolerability of Ascending Single Doses of Moxifloxacin, a New 8-Methoxy Quinolone, Administered to Healty Subjects, Anti. Agents Chem., 42(8): 2060-65 (1998) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0225: Fass, In Vitro Activity of Bay 12-8039, a New 8-Methoxyquinolone, Anti. Agents Chem., 41(8): 1818-24 (1997) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0228: Donnenfeld, ASCRS White Paper: Management of Infectious Keratitis Following Laser In Situ Keratomileusis, J. Cataract Refract. Surg., 31:2008-11 (2005) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0229: Solomon et al., Special Report, Infectious Keratitis After Laser In Situ Keratomileusis: Results of an ASCRS Survey, J. Cataract Refract. Surg., 29: Jun. 2001 (2003) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0232: Fraunfelder et al., Fatal Aplastic Anemia Following Topical Administration of Ophthalmic Chloramphenicol., Am. J. Ophthalmol., 93(3):356-60 (1982) in *Bayer Healthcare AG, Alcon, Inc and Alcon Research, Ltd. v. Teva Pharmaceuticals USA, Inc.* (Civil Action No. 06-234 SLR) (Plaintiffs' Exhibit List).
PTX0233: Fraunfelder and Meyer, Systemic Reactions to Ophthalmic Drug Preparations, Medical Toxicology, 2:287-93 (1987) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0242: Thibodeaux et al., Quantitative Comparison of Fluoroquinolone Therapies of Experimental Gram-Negative Bacterial Keratitis, Current Eye Research, 28(5):337-42 (2004) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0243: Aliprandis et al., Comparative Efficacy of Topical Moxifloxacin Versus Ciprofloxacin and Vancomycin in the Treatment of *P. aeruginosa* and Ciprofloxacin-Resistant MRSA Keratitis in Rabbits, Cornea 24(2):201-05 (2005) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0262: Compound Card for BAY Y6957 (with translation) (BL002-015187) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0264: Compound Card for BAY 12-8039 (with translation) (BL002-016090-016092) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0277-A: Updated Curriculum Vitae of Dr. Eduardo C. Alfonso (BA002-000001-00000055) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0281: Munir et al., Clinical Response of Contact Lens-Associated Fungal Keratitis to Topical Fluoroquinolone Therapy, Cornea 26(5):621-24 (2007) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0282: Alfonso and Miller, Impact of 4th Generation Fluoroquinolones on Growth Rate and Detection Time of Fungal Pathogens, Invest. Ophthalmology and Vis. Science, 46:2766-B319 (2005) (ARVO E-Abstract) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0304: Curriculum Vitae of Dr. Ashim K. Mitra in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0312: Schoenwald and Ward, Relationship between Steroid Permeability across Excised Rabbit Cornea and Octanol-Water Partition Coefficients, J. Pharm. Sci., 67(6):786-88 (1978) in *Bayer Healthcare AG, Alcon. Inc., and Alcon Research, Ltd. v. Teva Pharmaceuticals USA, Inc.* (Civil Action No. 06-234 SLR) (Plaintiffs' Exhibit List).
PTX0361 Email from Stroman to Hiddemen and Schlech re: Moxifloxacin Advantages (AL001-006984-006985) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0363: Evaluation of Moxifloxacin HCI [BAY 12-8039] (AL-15469A) (AL003-000163-000279) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0364: Excerpts from Alcon Laboratories Notebook # 10901 (AL010-001000-001065) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0365: Excerpts from Alcon Laboratories Notebook # 11030 (AL010-002000-002025) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0366: Exceprts from Alcon Laboratories Notebook # 13247 (AL010-003000-003059) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0386: Robertson at al., Absorption and Distribution of Moxifloxacin, Olfoxacin and Gatifloxacin into Ocular Tissues and Plasma Following Topical Ocular Administration to Pigmented Rabbits (2004 ARVo Poster) (AL009-000001) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0399: Letter from Alcon to Bayer requesting shipment of 10 grams of Moxifloxacin (AL001-004147) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX0402: Moxifloxacin screening agreement between Bayer and Nestle (AL001-004148-004154) in *Bayer Healthcare AG, Alcon,*

(56) References Cited

OTHER PUBLICATIONS

*Inc., and Alcon Research, Ltd. v. Teva Pharmaceuticals USA, Inc.* (Civil Action No. 06-234 SLR) (Plaintiffs' Exhibit List).
PTX1063: Excerpt of Physicians' Desk Reference 53rd Edition 1999: Alcon Ciloxan in *Bayer Healthcare AG, Alcon, Inc., and Alcoa Research, Ltd. v. Teva Pharmaceuticals USA, Inc.* (Civil Action No. 06-234 SLR) (Plaintiffs' Exhibit List).
PTX1065: Alcon's Research Compound Request for BAY 12-8039 (AL001-003945) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX1066: Weekly Status Report of Moxifloxacin Evaluation (AL001-000214-000215) in *Bayer Healthcare AG, Alcon, Inc., and Alcon Research, Ltd. v. Teva Pharmaceuticals USA, Inc.* (Civil Action No. 06-234 SLR) (Plaintiffs' Exhibit List).
PTX1096: Petersen, U., et al., "Synthesis and In Vitro Activity of BAY 12-8039, a New 8-Methoxyquinolone," (BL005-019300) in *Bayer Healthcare AG, Alcon, Inc., and Alcon Research, Ltd. v. Teva Pharmaceuticals USA, Inc.* (Civil Action No. 06-234 SLR).
PTX1099: Excerpt Opinion on Investigational Drugs, Zuranko at al., Oxazolidinone antibacterial agents: development of the clinical candidates eperezolid and linezolid, pp. 151-159 in *Bayer Healthcare AG, Alcon, Inc., and Alcon Research, Ltd. v. Teva Pharmaceuticals USA, Inc.* (Civil Action No. 06-234 SLR).
PTX1116: Alcon Data: Ex Vivo Corneal Penetration of Fluoroquinolones (AL007-038115-116) in *Bayer Healthcare AG, Alcon, Inc., and Alcon Research, Ltd. v. Teva Pharmaceuticals USA, Inc.* (Civil Action No. 06-234 SLR).
PTX1117: Solomon et al., Penetration of Topically Applied Gatifloxacin 0.3%, Moxifloxacin 0.5%, and Ciprofloxacin 0.3% into the Aqueous Humor, Ophthalmology 112 (3): 466-469 (Mar. 2005) in *Bayer Healthcare AG, Alcon, Inc., and Alcon Research, Ltd. v. Teva Pharmaceuticals USA, Inc.* (Civil Action No. 06-234 SLR).
PTX1119: Alcon Data: corneal Perfusion Chambers-Moxifloxacin Rate of Diffusion (Flux) (AL007-038117-038120) in *Bayer Healthcare AG, Alcon, Inc., and Alcon Research, Ltd. v. Teva Pharmaceuticals USA, Inc.* (Civil Action No. 06-234 SLR).
PTX1124. Dalhoff et al., In vitro Activity of BAY 12-8039, New 8-Methoxyquinolone, Chemother., 42:410-25 (1996) in *Bayer Healthcare AG, Alcon, Inc., and Alcon Research, Ltd. v. Teva Pharmaceuticals USA, Inc.* (Civil Action No. 06-234 SLR).
PTX1125: Schmitz et al., Relationship between Cirpofloxacin, Ofloxacin, Levofloxacin, Sparfloxacin and Moxifloxacin (BAY 12-8039) MICs and Mutations in grlA, GrlB, gyrA and gyrB in 116 Unrelated Clinical Isolates of *Staphylococcus aureus*, J. Anti. Chem., 41:481-84 (1998) in *Bayer Healthcare AG, Alcon, Inc., and Alcon Research, Ltd. v. Teva Pharmaceuticals USA, Inc.* (Civil Action No, 06-234 SLR).
PTX1126: Search Results: Table of contents, J. Antimlcro. Chem., 41(4) (1998) in *Bayer Healthcare AG, Alcon, Inc., and Alcon Research, Ltd. v. Teva Pharmaceuticals USA, Inc.* (Civil Action no. 06-234 SLR).
PTX2018: Powerpoint slide—Person of Ordinary Skill for the '830 Patent in *Bayer Healthcare AG, Alcon, Inc., and Alcon Research, Ltd. v. Teva Pharmaceuticals USA, Inc.* (Civil Action No. 06-234 SLR).
PTX2019: Powerpoint slide—Requirements in 1998 for New Ophthalmic Compositions in *Bayer Healthcare AG, Alcon, Inc., and Alcon Research, Ltd. v. Teva Pharmaceuticals USA, Inc.* (Civil Action No. 06-234 SLR).
PTX2021: Powerpoint slide—Moxifloxacin Flux at Different Concentrations in *Bayer Healthcare AG, Alcon, Inc., and Alcon Research, Ltd. v. Teva Pharmaceuticals USA, Inc.* (Civil Action No. 06-234 SLR).
PTX2025: Powerpoint slide—Other Quinolones in *Bayer Healthcare AG, Alcon, Inc., and Alcon Research, Ltd. v. Teva Pharmaceuticals USA, Inc.* (Civil Action No. 06-234 SLR).
PTX2030A: Powerpoint slide—Anterior Segment of the Eye in *Bayer Healthcare AG, Alcon, Inc., and Alcon Research, Ltd. v. Teva Pharmaceuticals USA, Inc.* (Civil Action No. 06-234 SLR).
PTX2030B: Powerpoint slide—Tear Film in *Bayer Healthcare AG, Alcon, Inc., and Alcon Research, Ltd. v. Teva Pharmaceuticals USA, Inc.* (Civil Action No. 06-234 SLR).
PTX2030C: Powerpoint slide—Cornea in *Bayer Healthcare AG, Alcon, Inc., and Alcon Research, Ltd. v. Teva Pharmaceuticals USA, Inc.* (Civil Action No. 06-234 SLR).
PTX2030E: Powerpoint slide—Aqueous Humor in *Bayer Healthcare AG, Alcon, Inc., and Alcon Research, Ltd. v. Teva Pharmaceuticals USA, Inc.* (Civil Action No. 06-234 SLR).
PTX2030F: Powerpoint slide—Aqueous Humor in *Bayer Healthcare AG, Alcon, Inc., and Alcon Research, Ltd. v. Teva Pharmaceuticals USA, Inc.* (Civil Action No. 06-234 SLR).
PTX2030G: Powerpoint slide Aqueous Turnover in *Bayer Healthcare AG, Alcon, Inc., and Alcon Research, Ltd. v. Teva Pharmaceuticals USA, Inc.* (Civil Action No. 06-234 SLR).
PTX2030H: Powerpoint slide—Some Compounds Are Maintained Longer in the Aqueous Humor in *Bayer Healthcare AG, Alcon, Inc., and Alcon Research, Ltd. v. Teva Pharmaceuticals USA, Inc.* (Civil Action No. 06-234 SLR).
Stroman et al, "In Vitro and In Vivo Potency of Moxifloxacin and Moxifloxacin Ophthalmic Solution 0.5%, A New Topical Fluoroquinolone", Survey of Opthalmology, vol. 50, No. 6, Nov. 1, 2005.
Robertson et al, "Ocular Pharmacokinetics of Moxifloxacin After Topical Treatment of Animals and Humans" Survey of Ophthalmology, vol. 50, No. 6, Nov. 1, 2005.
Francois et al., "Ocular Infection Due to Gram Negative and Non-Fermentative Microorganisms", Database embase [on-line] Elsevier Science Publishers, Amsterdam, NL, 1972, vol. 3, No. 2, 1972, pp. 114-121.
Thiel et al., "Adherence and Pathogenesis of *Staphylococcus Aureus* and *Pseudomonas Aeruginosa* in Corneal Infections", Experimental Eye Research, Academic Press Ltd., London, vol. 55, Sep. 1, 1992, p. 208.
European Search Report for EP 10176412 mailed Nov. 10, 2010.
European Search Report for EP 10178657 mailed Jan. 28, 2011.
Blondeau, Joseph M., A review of the comparative in-vitro activities of 12 antimicrobial agents, with focus on five new 'respiratory quinolones', *Journal of Antimicrobial Chemotherapy*, vol. 43, Suppl. B, pp. 1-11 (1999).
Elies, W., "Newer fluoroquinolones in the treatment of ENT infections", *Chemotherapie Journal*, 7/3, pp. 93-97 (1998) (no translation); XP000892813.
Ernst et al., "Levofloxacin and trovafloxacin: The next generation of fluoroquinolones?", *Clinical Review, Am. J. Health-Syst. Pharm.*, vol. 54, pp. 2569-2584 (114/15/97).
Gootz et al., "Fluoroquinolone antibacterials: SAR mechanism of action, resistance, and clinical aspects", *Medicinal Research Reviews*, vol. 16, pp. 433-486 (1996).
Kaw et al., "The penetration of trovafloxacin into the eye and CSF of rabbits", IOVS, vol. 40, No. 4, p. S88 (Mar. 15, 1999); XP-000892619.
Kraseman et al., "Efficacy of Moxifloxacin against *Staphylococcus aureus* in respiratory tract and skin and skin structure infections", *Jornal of Antimicrobial Chemotherapy*, vol. 44, No. Suppl. A, pp. 150 (Jul. 1999); XP000892776.
McLeod et al., "The effect of topical trovafloxacin in a rabbit *Streptococcus pneumoniae* keratitis model", IOVS vol. 40, No. 4, p. S689 (Mar. 15, 1999) XP-000892625.
NCCLS Document M7-A4, "Methods for Dilution Antimicrobial Susceptibility Tests for Bacteria That Grow Aerobically", 4th Edition.
"New Antimicrobial Agents Approved by the U.S. Food and Drug Administration in 1997 and New Indications for Previously Approved Agents" *Antimicrobial Agents and Chemotherapy*, vol. 42, No. 4, pp. 987-988 (Apr. 1, 1998); XP000872060.
Ng et al., "Treatment of experimental *Staphylococcus epidermidis* endophthalmitis with oral trovafloxacin" *American Journal of Ophthalmology*, vol. 216 (2), pp. 278-287 (Aug. 1998).
Patent Abstracts of Japan, vol. 1998, No. 10 (Aug. 31, 1998), JP 10 130148 May 19, 1998 abstract.
Patent Abstracts of Japan, vol. 012, No. 472 (Dec. 9, 1988), JP 63 190826 Aug. 8, 1988 abstract.

(56) References Cited

OTHER PUBLICATIONS

Pediatric Research, 104th Annual Meeting of the American Pediatric Society and the 63rd Annual meeting of the Society for Pediatric Research, vol. 35, No. 4, Part 2, p. 191A, Seattle, Washington (May 2-5, 1994).

Senturia, Ben, "Etiology of External Otitis", *Larynyoscope*, vol. 55, pp. 277-293 (1945).

Tillotson, G. S., "Quinolones: structure-activity relationships and future predictions", *J. of Medical Microbiology*, vol. 44, pp. 320-324 (1996).

Vincent et al., "Pharmacokinetics and safety of trovafloxacin in healthy male volunteers following administration of single intravenous doses of the prodrug, alatrofloxacin", *Journal of Antimicrobial Chemotherapy*, vol. 39, Suppl. B, pp. 75-80 (Jan. 1, 1997).

Weiss, Lee R., "Therapeutic Pathways for Antimicrobial Use: General Overview", *The American Journal of Managed Care*, vol. 4, No. 10, Sup., pp. S543-S549 (1988).

Wentland, Mark P., "Structure-activity relationships of fluoroquinolones", *The New Generation of Quinolones*, (Siporin, C., Heifetz, C. L. & Domagala, J. M., Eds), pp. 1-43, Marcel Dekker, New York (1990).

Goldstein, et al., "In Vitro Activity of Bay 12-8039, a New 8-Methoxyquinolone, Compared to the Activities of 11 Other Oral Antimicrobial Agents Against 390 Aerobic and Anaerobic Bacteria Isolated from Human and Animal Bite Wound Skin and Soft Tissue Infections in Humans", *Antimicrobial Agents and Chemotherapy*, Jul. 1997, pp. 1552-1557.

Goldstein, et al., "Comparative In Vitro Activities of Azithromycin, Bay y 3118, Levofloxacin, Sparfloxacin, and 11 Other Orgal Antimicrobial Agents Against 194 Aerobic and Anerobic Bite Wound Isolates", *Antimicrobial Agents and Chemotherapy*, May 1995, pp. 1097-1100.

Rubinstein, "Pharmacology—Tissue Distribution", *International Moxifloxacin Symposium*, $1^{st}$ (2000) Meeting date 1999, pp. 130-133; Editors: Mandell, Lionel.

METHOD OF TREATING OTIC INFECTIONS WITH MOXIFLOXACIN COMPOSITIONS

This application is a continuation of U.S. application Ser. No. 10/715,055, filed Nov. 17, 2003, which is a continuation of U.S. application Ser. No. 10/200,868, filed Jul. 22, 2002, now U.S. Pat. No. 6,716,830, which is a continuation of U.S. patent application Ser. No. 09/646,797, filed Sep. 22, 2000, now abandoned, which is the National Stage of International Application No. PCT/US99/22622, filed Sep. 29, 1999, which claims benefit under 35 U.S.C. §119(e) of U.S. Provisional Application Nos. 60/102,504 and 60/102,506, filed on Sep. 30, 1998.

BACKGROUND OF THE INVENTION

The present invention is directed to the provision of topical antibiotic pharmaceutical compositions for the treatment of ophthalmic, otic and nasal infections, particularly bacterial infections, and to methods of treating ophthalmic, otic and nasal infections by applying those compositions to the affected tissues. The compositions and methods of the invention are based on the use of a new class of antibiotics. The compositions of the present invention may also contain one or more anti-inflammatory agents.

The use of quinolone antibiotics to treat infections represents the current state of the art in the field of ophthalmic pharmaceutical compositions and methods of treatment. For example, a topical ophthalmic composition containing the quinolone ciprofloxacin is marketed by Alcon Laboratories, Inc. under the name CILOXAN™ (Ciprofloxacin 0.3%) Ophthalmic Solution. The following quinolones have also been utilized in ophthalmic antibiotic compositions:

| Quinolone | Product | Manufacturer |
|---|---|---|
| Ofloxacin | OCUFLOX ™ | Allergan |
| Norfloxacin | CHIBROXIN ™ | Merck |
| Lomefloxacin | LOMEFLOX ™ | Senju |

The foregoing quinolone antibiotic compositions are generally effective in treating ophthalmic infections, and have distinct advantages over prior ophthalmic antibiotic compositions, particularly those having relatively limited spectrums of antimicrobial activity, such as: neomycin, polymyxin B, gentamicin and tobramycin, which are primarily useful against gram negative pathogens; and bacitracin, gramicidin, and erythromycin, which are primarily active against gram positive pathogens. However, despite the general efficacy of the ophthalmic quinolone therapies currently available, there is a need for improved compositions and methods of treatment based on the use of antibiotics that are more effective than existing antibiotics against key ophthalmic pathogens, and less prone to the development of resistance by those pathogens.

There is an even greater need for effective topical compositions and methods for treating otic and nasal infections, particularly bacterial infections. The use of oral antibiotics to treat otic infections in children has limited efficacy, and creates a serious risk of pathogen resistance to the orally administered antibiotics.

Ophthalmic, otic and nasal infections are frequently accompanied by inflammation of the infected ophthalmic, otic and nasal tissues and perhaps even surrounding tissues. Similarly, ophthalmic, otic and nasal surgical procedures that create a risk of microbial infections frequently also cause inflammation of the affected tissues. Thus, there is also a need for ophthalmic, otic and nasal pharmaceutical compositions that combine the anti-infective activity of one or more antibiotics with the anti-inflammatory activity of one or more steroid or non-steroid agents in a single composition.

SUMMARY OF THE INVENTION

The invention is based on the use of a potent new class of antibiotics to treat ophthalmic, otic and nasal infections, as well as the prophylactic use of these antibiotics following surgery or other trauma to ophthalmic, otic or nasal tissues. The compositions of the present invention may also be administered to the affected tissues during ophthalmic, otic or nasal surgical procedures to prevent or alleviate post-surgical infection.

The compositions preferably also contain one or more anti-inflammatory agents to treat inflammation associated with infections of ophthalmic, otic or nasal tissues. The anti-inflammatory component of the compositions is also useful in treating inflammation associated with physical trauma to ophthalmic, otic or nasal tissues, including inflammation resulting from surgical procedures. The compositions of the present invention are therefore particularly useful in treating inflammation associated with trauma to ophthalmic, otic or nasal tissues wherein there is either an infection or a risk of an infection resulting from the trauma.

Examples of ophthalmic conditions that may be treated with the compositions of the present invention include conjunctivitis, keratitis, blepharitis, dacryocystitis, hordeolum and corneal ulcers. The compositions of the invention may also be used prophylactically in connection with various ophthalmic surgical procedures that create a risk of infection.

Examples of otic conditions that may be treated with the compositions of the present invention include otitis externa and otitis media. With respect to the treatment of otitis media, the compositions of the present invention are primarily useful in cases where the tympanic membrane has ruptured or tympanostomy tubes have been implanted. The compositions may also be used to treat infections associated with otic surgical procedures, such as tympanostomy, or to prevent such infections.

The compositions of the present invention are specially formulated for topical application to ophthalmic, otic and nasal tissues. The compositions are preferably sterile, and have physical properties (e.g., osmolality and pH) that are specially suited for application to ophthalmic, otic and nasal tissues, including tissues that have been compromised as the result of preexisting disease, trauma, surgery or other physical conditions.

DETAILED DESCRIPTION OF THE INVENTION

The antibiotics used in the compositions and methods of the present invention have the following formula:

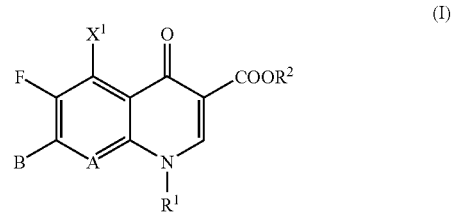

wherein:
A is CH, CF, CCl, C—OCH$_3$, or N;
X$^1$ is H, halogen, NH$_2$, or CH$_3$;
R$^1$ is C$_1$ to C$_3$ alkyl, FCH$_2$CH$_2$, cyclopropyl or phenyl, optionally mono-, di- or tri-substituted by halogen, or A and R$_1$ together can form a bridge of formula C—O—CH$_2$—CH(CH$_3$);
R$^2$ is H, C$_1$ to C$_3$ alkyl (optionally substituted by OH, halogen or NH$_2$), or 5-methyl-2-oxo-1,3-dioxol-4-yl-methyl; and
B is a selected from the group consisting of:

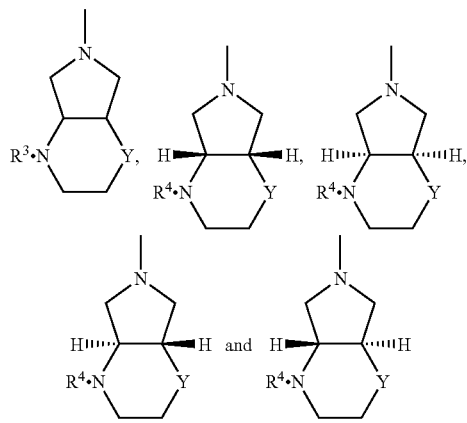

wherein:
Y is O or CH$_2$;
R$^3$ is C$_2$-C$_5$ alkoxyl, CH$_2$—CO—C$_6$H$_5$, CH$_2$CH$_2$CO$_2$R', R'O$_2$C—CH═C—CO$_2$R', CH═CH—CO$_2$R' or CH$_2$CH$_2$—CN,
wherein:
R' is H or C$_1$ to C$_3$ alkyl;
R$^4$ is H, C$_1$ to C$_3$ alkyl, C$_2$-C$_5$ alkoxyl, CH$_2$—CO—C$_6$H$_5$, CH$_2$CH$_2$CO$_2$R', R'O$_2$C—CH═C—CO$_2$R', CH═CH—CO$_2$R', CH$_2$CH$_2$—CN or 5-methyl-2-oxo-1,3-dioxol-4-yl-methyl,
wherein:
R' is H or C$_1$ to C$_3$ alkyl; and
their pharmaceutically useful hydrates and salts.

The compound Moxifloxacin is most preferred. Moxifloxacin has the following structure:

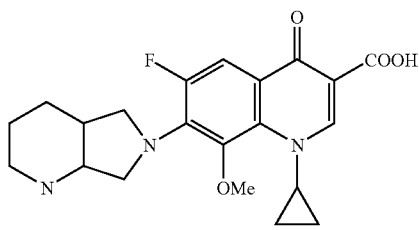 [SMILES: COc1c(N2CC3CCCNC3C2)c(F)cc2c(=O)c(C(=O)O)cn(C3CC3)c12]

Further details regarding the structure, preparation, and physical properties of Moxifloxacin and other compounds of formula (I) are provided in U.S. Pat. No. 5,607,942.

The concentrations of the antibiotics of formula (I) in the compositions of the present invention will vary depending on the intended use of the compositions (e.g., treatment of existing infections or prevention of post-surgical infections), and the relative antimicrobial activity of the specific antibiotic selected. The antimicrobial activity of antibiotics is generally expressed as the minimum concentration required to inhibit the growth of a specified pathogen. This concentration is also referred to as the "minimum inhibitory concentration" or "MIC". The term "MIC90" refers to the minimum concentration of antibiotic required to inhibit the growth of ninety percent (90%) of the strains of a species. The concentration of an antibiotic required to totally kill a specified bacteria is referred to as the "minimum bactericidal concentration" or "MBC". The minimum inhibitory concentration of Moxifloxacin for several bacteria commonly associated with ophthalmic, otic and nasal infections are provided in the following table:

| Microorganism | MIC$_{90}$ |
| --- | --- |
| S. aureus/methicillin sensitive | 0.13 |
| S. aureus/methicillin resistant | 4.0 |
| S. aureus/quinolone resistant | 4.0 |
| S. epidermidis/methicillin sensitive | 0.25 |
| S. epidermidis/methicillin resistant | 4.0 |
| S. pneumoniae/penicillin sensitive | 0.25 |
| S. pneumoniae/penicillin resistant | 0.25 |
| P. aeruginosa | 8.0 |
| H. influenzae/.beta.-lactamase positive | 0.06 |
| H influenzae/.beta.lactamase negative | 0.06 |

All of the foregoing concentrations are expressed as micrograms per milliliter ("mcg/ml").

The appropriate antibiotic concentration for ophthalmic compositions will generally be an amount of one or more antibiotics of formula (I) sufficient to provide a concentration in the aqueous humor and lacrimal fluid of the eye equal to or greater than the MIC90 level for the selected antibiotic(s), relative to gram-negative and gram-positive organisms commonly associated with ophthalmic infections. The appropriate concentration for otic and nasal compositions will generally be an amount of one or more antibiotics of formula (I) sufficient to provide a concentration in the infected tissues equal to or greater than the MIC90 level for the selected antibiotic(s), relative to gram-negative and gram-positive organisms commonly associated with otic or nasal infections. Such amounts are referred to herein as "an antimicrobial effective amount". The compositions of the present invention will typically contain one or more compounds of formula (I) in a concentration of from about 0.1 to about 1.0 percent by weight ("wt. %") of the compositions.

The compositions of the present invention may also contain one or more anti-inflammatory agents. The anti-inflammatory agents utilized in the present invention are broadly classified as steroidal or non-steroidal. The preferred steroidal anti-inflammatory agents are glucocorticoids.

The preferred glucocorticoids for ophthalmic and otic use include dexamethasone, loteprednol, rimexolone, prednisolone, fluorometholone, and hydrocortisone. The preferred glucocorticoids for nasal use include mometasone, fluticasone, beclomethasone, flunisolide, triamcinolone and budesonide.

The dexamethasone derivatives described in U.S. Pat. No. 5,223,493 (Boltralik) are also preferred steroidal anti-inflammatory agents, particularly with respect to compositions for treating ophthalmic inflammation. The following compounds are especially preferred:

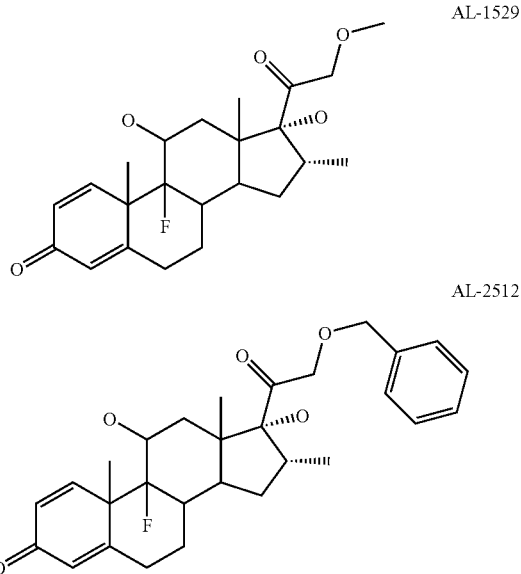

These compounds are referred to herein as "21-ether derivatives of dexamethasone". The 21-benzyl ether derivative (i.e., compound AL-2512) is particularly preferred.

The preferred non-steroidal anti-inflammatory agents are: prostaglandin H synthetase inhibitors (Cox I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; inhibitors of cytokine production, such as inhibitors of the NFkB transcription factor; or other anti-inflammatory agents known to those skilled in the art.

The concentrations of the anti-inflammatory agents contained in the compositions of the present invention will vary based on the agent or agents selected and the type of inflammation being treated. The concentrations will be sufficient to reduce inflammation in the targeted ophthalmic, otic or nasal tissues following topical application of the compositions to those tissues. Such an amount is referred to herein as "an anti-inflammatory effective amount." The compositions of the present invention will typically contain one or more anti-inflammatory agents in an amount of from about 0.01 to about 1.0 wt. %.

The compositions are typically administered to the affected ophthalmic, otic or nasal tissues by topically applying one to four drops of a sterile solution or suspension, or a comparable amount of an ointment, gel or other solid or semisolid composition, one to four times per day. However, the compositions may also be formulated as irrigating solutions that are applied to the affected ophthalmic, otic or nasal tissues during surgical procedures.

The ophthalmic, otic and nasal compositions of the present invention will contain one or more compounds of formula (I) and preferably one or more anti-inflammatory agents, in pharmaceutically acceptable vehicles. The compositions will typically have a pH in the range of 4.5 to 8.0. The ophthalmic compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

Ophthalmic, otic and nasal pharmaceutical products are typically packaged in multidose form. Preservatives are thus required to prevent microbial contamination during use. Suitable preservatives include: polyquatemium-1, benzalkonium chloride, thimerosal, chlorobutanol, methyl paraben, propyl paraben, phenylethyl alcohol, edetate disodium, sorbic acid, or other agents known to those skilled in the art. The use of polyquatemium-1 as the antimicrobial preservative is preferred. Typically such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically such co-solvents are employed at a level of from 0.01% to 2% by weight.

The use of viscosity enhancing agents to provide the compositions of the invention with viscosities greater than the viscosity of simple aqueous solutions may be desirable to increase ocular absorption of the active compounds by the target tissues or increase the retention time in the eye, ear or nose. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

The following examples are provided to further illustrate the ophthalmic, otic and nasal compositions of the present invention.

EXAMPLE 1

| Ophthalmic/Otic/Nasal Solution | |
|---|---|
| Ingredient | Amount (wt. %) |
| Moxifloxacin | 0.35 |
| Sodium Acetate | 0.03 |
| Acetic Acid | 0.04 |
| Mannitol | 4.60 |
| EDTA | 0.05 |
| Benzalkonium Chloride | 0.006 |
| Water | q.s. 100 |

EXAMPLE 2

| Ophthalmic/Otic/Nasal Suspension | |
|---|---|
| Ingredient | Amount (wt. %) |
| Moxifloxacin | 0.3 |
| Dexamethasone, Micronized USP | 0.10 |
| Benzalkonium Chloride | 0.01 |
| Edetate Disodium, USP | 0.01 |
| Sodium Chloride, USP | 0.3 |
| Sodium Sulfate, USP | 1.2 |
| Tyloxapol, USP | 0.05 |
| Hydroxyethylcellulose | 0.25 |
| Sulfuric Acid and/or Sodium Hydroxide, NF | q.s. for pH adjustment to 5.5 |
| Purified Water, USP | q.s. to 100 |

EXAMPLE 3

| Ophthalmic Ointment | |
|---|---|
| Ingredient Amount | (wt. %) |
| Moxifloxacin | 0.35 |
| Mineral Oil, USP | 2.0 |
| White petrolatium, USP | q.s 100 |

EXAMPLE 4

| Ophthalmic Ointment | |
|---|---|
| Ingredient | Amount (wt. %) |
| Moxifloxacin | 0.3 |
| Fluorometholone Acetate, USP | 0.1 |
| Chlorobutanol, Anhydrous, NF | 0.5 |
| Mineral Oil, USP | 5 |
| White Petrolatum, USP | q.s. 100 |

The invention has been described herein by reference to certain preferred embodiments. However, as obvious variations thereon will become apparent to those skilled in the art, the invention is not to be considered as limited thereto.

What is claimed is:

1. A method of treating otic infections commonly associated with at least one of *P. aeruginosa* and *H. influenzae*, which comprises topically applying to the affected otic tissue a therapeutically effective amount of a topical otic pharmaceutical composition comprising moxifloxacin or a pharmaceutically useful hydrate or salt thereof at a concentration of 0.1 to 1.0 wt. % and a pharmaceutically acceptable vehicle therefor.

2. A method of treating otic infections commonly associated with at least one of *P. aeruginosa* and *H. influenzae* and attendant inflammation, which comprises topically applying to the affected otic tissue a therapeutically effective amount of a topical otic pharmaceutical composition comprising moxifloxacin or a pharmaceutically useful hydrate or salt thereof at a concentration of 0.1 to 1.0 wt. %, an anti-inflammatory effective amount of a steroidal or non-steroidal anti-inflammatory agent, and a pharmaceutically acceptable vehicle therefor.

3. A method according to claim 2, wherein the anti-inflammatory agent comprises a glucocorticoid.

4. A method according to claim 3, wherein the glucocorticoid is selected from the group consisting of dexamethasone, rimexolone, prednisolone, fluorometholone, hydrocortisone, mometasone, fluticasone, beclomethasone, flunisolide, triamcinolone and budesonide.

5. A method according to claim 2, wherein the anti-inflammatory agent comprises a non-steroidal agent selected from the group consisting of prostaglandin H synthetase inhibitors, PAF antagonists, and PDE IV inhibitors.

6. A method according to claim 2, wherein the anti-inflammatory agent comprises dexamethasone.

7. A method according to claim 2, wherein the anti-inflammatory agent comprises nepafenac.

8. A topical composition method according to any one of claims 1, 2, 6 or 7, wherein the composition contains moxifloxacin or a pharmaceutically useful hydrate or salt thereof at a concentration of about 0.35 wt. %.

9. A method according to any one of claims 1, 2, 6, and 7, wherein the composition contains moxifloxacin or a pharmaceutically useful hydrate or salt thereof at a concentration of 0.35 to 1 wt. %.

* * * * *